(12) United States Patent
McMillen et al.

(10) Patent No.: US 7,876,093 B2
(45) Date of Patent: Jan. 25, 2011

(54) EDDY CURRENT INSPECTION DEVICE, PROXIMITY PROBE AND METHOD FOR ASSEMBLING AN EDDY CURRENT INSPECTION DEVICE

(75) Inventors: Christopher Charles McMillen, Carson City, NV (US); Andrew David Bell, Carson City, NV (US)

(73) Assignee: General Electric Company, Schenectady, NY (US)

( * ) Notice: Subject to any disclaimer, the term of this patent is extended or adjusted under 35 U.S.C. 154(b) by 531 days.

(21) Appl. No.: 11/999,706

(22) Filed: Dec. 6, 2007

(65) Prior Publication Data

US 2009/0146655 A1  Jun. 11, 2009

(51) Int. Cl.
  *G01B 7/14* (2006.01)
(52) U.S. Cl. .................. 324/207.26; 324/236
(58) Field of Classification Search ............. 324/207.26
  See application file for complete search history.

(56) References Cited

U.S. PATENT DOCUMENTS

| | | | |
|---|---|---|---|
| 4,408,159 A * | 10/1983 | Prox ...................... 324/207.12 |
| 4,419,646 A * | 12/1983 | Hermle ........................ 336/90 |
| 5,998,988 A * | 12/1999 | Dickmeyer et al. ......... 324/174 |
| 6,377,040 B1 | 4/2002 | Hell |
| 6,693,425 B2 | 2/2004 | Wache |
| 7,012,425 B2 | 3/2006 | Shoji |
| 7,078,895 B1 | 7/2006 | Shoji |
| 7,154,265 B2 | 12/2006 | Togo et al. |
| 7,235,967 B2 | 6/2007 | Nishimizu et al. |
| 7,256,577 B2 | 8/2007 | Linn et al. |
| 7,295,004 B2 | 11/2007 | Kroner |
| 7,304,474 B2 | 12/2007 | Rempt |
| 7,489,217 B2 * | 2/2009 | Rohrig et al. ................ 335/205 |
| 2001/0019262 A1* | 9/2001 | Woolsey et al. ........ 324/207.26 |
| 2002/0145421 A1* | 10/2002 | Rose ..................... 324/207.26 |
| 2006/0038558 A1 | 2/2006 | Rempt et al. |

* cited by examiner

*Primary Examiner*—Jay M Patidar
(74) *Attorney, Agent, or Firm*—Armstrong Teasdale LLP

(57) ABSTRACT

A method for assembling an eddy current inspection device includes at least partially positioning a first tip assembly within a cavity defined by a proximity probe case. The first tip assembly defines a bore therethrough. The first tip assembly is sealingly coupling to the proximity probe case. A second tip assembly is at least partially positioned within the cavity and sealingly coupled to the first tip assembly.

20 Claims, 1 Drawing Sheet

EDDY CURRENT INSPECTION DEVICE, PROXIMITY PROBE AND METHOD FOR ASSEMBLING AN EDDY CURRENT INSPECTION DEVICE

BACKGROUND OF THE INVENTION

This invention relates generally to eddy current probes and, more particularly, to methods and apparatus for sealing eddy current transducer components within an eddy current probe.

Eddy current (EC) inspection devices may be used to detect abnormalities and/or defects in a component, such as a rotating machinery component. At least one known EC inspection device is used to detect a distance to a shaft during rotation. If a relatively large variation is detected, an alarm signal is activated. Other known EC inspection devices are used to detect cracks, pings, dings, raised material, and/or other surface imperfections on a surface of the component, and/or to evaluate material properties of the component including the conductivity, density, and/or degrees of heat treatment of the component.

During operation, known EC devices measure the interaction between an electromagnetic field generated by the EC device and the component being tested. For example, known EC devices include a sensing coil that generates a magnetic field. When the sensing coil is positioned adjacent to a conductive component, an eddy current is generated on the surface of the component. A flaw on and/or near the surface of the component generates a disruption in the eddy current field, which produces a secondary magnetic field that is detected by the sensing coil. The secondary magnetic field is converted into an electrical signal that is transmitted to a strip chart recorder, for example, and recorded.

An eddy current probe typically includes a tip assembly, a probe cable and a probe case. The tip assembly packages a sensing coil that is electrically interfaced with or coupled to the probe cable. Typically, a single O-ring seal is positioned at the interface to prevent or limit undesirable liquid leakage into the tip assembly and/or the probe case at the interface. Known EC inspection devices for underwater applications may also include a swage-type fitting that sealingly couples a protective tube about the probe cable and to the probe case to prevent or limit undesirable exposure of the tip assembly and the probe case to a pressurized liquid environment.

While inspecting rotating machinery components in pressurized liquid applications, pressurized liquid, such as water or a lubricant, may enter into the tip assembly and undesirable contact the sensing coil of an eddy current transducer. The liquid may enter through the probe case and into the tip assembly and/or liquid may enter into the probe cable through openings defined in the probe cable.

BRIEF DESCRIPTION OF THE INVENTION

In one aspect, a method for assembling an eddy current inspection device is provided. The method includes at least partially positioning a first tip assembly within a cavity defined by a proximity probe case. The first tip assembly defines a bore therethrough. The first tip assembly is sealingly coupled to the proximity probe case. A second tip assembly is at least partially positioned within the cavity. The second tip assembly is sealingly coupled to the first tip assembly.

In another aspect, a proximity probe is provided. The proximity probe is coupled in communication with an electronic circuit and positionable adjacent a rotating machinery component and configured to generate a signal indicative of a gap between rotating machinery components. The proximity probe includes a case defining a cavity. A first tip assembly is at least partially positioned within the cavity and sealingly coupled to the case. A second tip assembly is coupled to a probe cable and at least partially positioned within the cavity. The second tip assembly is sealingly coupled to the first tip assembly.

In another aspect, an eddy current (EC) inspection device for use with rotating machinery components is provided. The EC inspection device includes a proximity probe coupled in communication with an electronic circuit and positionable adjacent the rotating machinery component. The proximity probe is configured to produce eddy currents to generate a signal indicative of a gap between rotating machinery components. The proximity probe includes a proximity probe case defining a cavity. A first tip assembly is at least partially positioned within the cavity and sealingly coupled to the proximity probe case. A second tip assembly is coupled to a probe cable and at least partially positioned within the cavity. The second tip assembly is sealingly coupled to the first tip assembly.

DETAILED DESCRIPTION OF THE INVENTION

Figure 1:
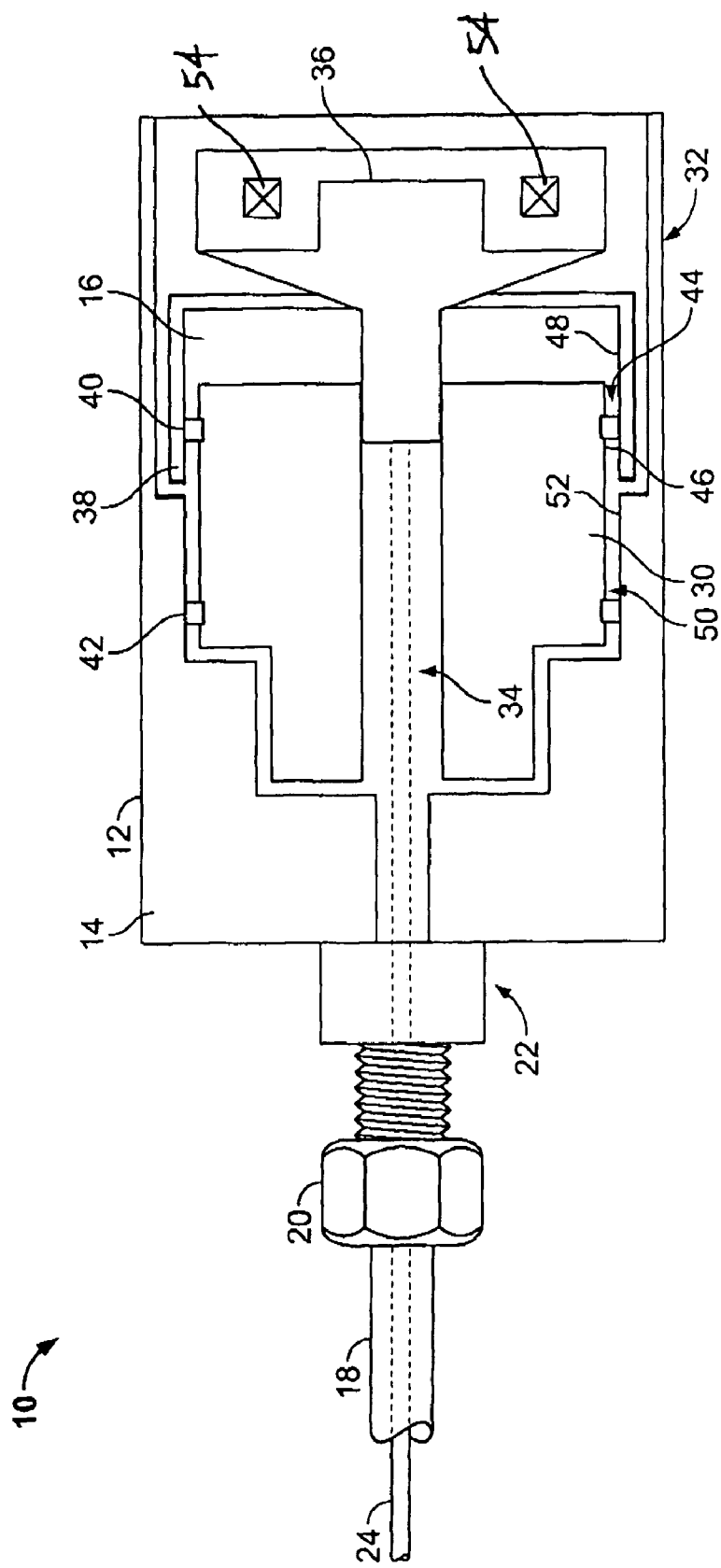
FIG. 1 is a cross-sectional view of an exemplary eddy current probe.

The present invention provides an eddy current inspection device or probe suitable for use in pressurized environments, such as pressurized liquid or underwater environments, to inspect and/or monitor rotating machinery components, such as at a hydroelectric power dam. The eddy current inspection device includes an eddy current proximity probe having a plurality of tip assemblies positioned within a probe case or housing. Suitable sealing components, such as O-ring seals, are positioned about one or more of the tip assemblies to sealingly couple the tip assemblies within the probe case and prevent or limit undesirable pressurized liquid leakage into the probe case at an interface between tip assemblies and/or at an interface between the tip assemblies and the probe case.

The present invention is described below in reference to its application in connection with, and operation of, an eddy current inspection device or probe suitable for use in a pressurized liquid environment, such as in an underwater environment at a hydroelectric power dam, to inspect and/or monitor rotating machinery components. However, it should be apparent to those skilled in the art and guided by the teachings herein provided that the eddy current inspection device or probe as described herein is likewise suitable for inspecting and/or monitoring rotating and/or stationary components of any suitable machinery in any suitable environment. For example, the present invention may be used to inspect and/or monitor components used within a steam turbine, a gas turbine, a nuclear power plant, a hydroelectric power dam, or rotating machinery components in pressurized liquid or underwater environments.

FIG. 1 is a cross-sectional view of an exemplary eddy current (EC) inspection device or probe 10. In one embodiment, inspection device 10 is configured to inspect and/or monitor rotating machinery components, for example, rotating machinery components at a hydroelectric power dam. Inspection device 10 includes a proximity probe 12 including a proximity probe case or housing 14 that defines a cavity 16. Proximity probe 12 is coupled in communication with an electronic circuit (not shown) and is positioned near or adjacent to the rotating machinery component to inspect and/or monitor the vibrational characteristics and/or rotor position characteristics of the component. Proximity probe 12 is configured to produce eddy currents to generate a signal indicative of a gap or space between rotating machinery components, such as a gap or space between a rotating shaft and an inductor (not shown).

A protective tube 18, such as a tube made of a polymeric, metal or other suitable material, is coupled to probe case 14. In the exemplary embodiment, a swage-type fitting 20 sealingly couples tube 18 to a first end portion 22 of probe case 14. In alternative embodiments, any suitable coupling mechanism or component may be used to sealingly couple tube 18 to probe case 14. A probe cable 24 extends through tube 18 and fitting 20 into cavity 16.

A first tip assembly 30 is at least partially positioned within cavity 16 and is sealingly coupled to probe case 14 at a second end 32 of probe case 14. First tip assembly 30 defines a bore 34 through which probe cable 24 extends. In the exemplary embodiment, proximity probe 12 includes a second tip assembly 36 at least partially positioned within cavity 16 at second end 32 of probe case 14 and coupled to probe cable 24. Second tip assembly 36 is seated within bore 34 and is sealingly coupled to first tip assembly 30. In the exemplary embodiment, second tip assembly 36 includes a circumferential flange 38 that is coupled, such as welded, against a corresponding outer circumferential surface of first tip assembly 30. In an alternative embodiment, circumferential flange 38 is frictionally fitted against a corresponding outer circumferential surface of first tip assembly 30.

In the exemplary embodiment, at least one suitable sealing component, such as O-ring seal 40, is positioned about first tip assembly 30 to facilitate sealing a space or gap 44 defined between an outer surface 46 of first tip assembly 30 and an inner wall surface 48 of second tip assembly 36 to facilitate preventing or limiting undesirable pressurized liquid leakage into cavity 16. Additionally, at least one suitable sealing component, such as O-ring seal 42, is positioned about first tip assembly 30 to facilitate sealing a space or gap 50 defined between outer surface 46 and an inner wall surface 52 of probe case 14 defining cavity 16 to facilitate preventing or limiting undesirable pressurized liquid leakage into cavity 16. Such leakage may damage proximity probe components housed within cavity 16, such as a sensing coil of an eddy current transducer 54.

In one embodiment, first tip assembly 30 is at least partially positioned within cavity 16. First tip assembly 30 defines a bore 34 therethrough. First tip assembly 30 is sealing coupled to proximity probe case 14. In one embodiment, at least one sealing component, such as at least one O-ring 42, is positioned about first tip assembly 30 to facilitate sealing space 50 defined between outer circumferential surface 46 of first tip assembly 30 and inner wall surface 52 of proximity probe case 14. Second tip assembly 36 is positioned within cavity 16 and is sealingly coupled to first tip assembly 30 using one or more suitable sealing component. In a particular embodiment, second tip assembly 36 is at least partially seated within bore 34. At least one sealing component, such as at least one O-ring 40, is positioned about first tip assembly 30 to facilitate sealing space 44 defined between outer circumferential surface 46 of first tip assembly 30 and inner wall surface 48 of second tip assembly 36 at flange 38.

In one embodiment, flange 38 of second tip assembly 36 is coupled, such as welded or frictionally fitted, against outer surface 46 of first tip assembly 30. As shown in FIG. 1, probe cable 24 extends through bore 34 and is coupled to second tip assembly 36. Protective tube 18 is sealingly coupled to probe case 14 and probe cable 24 is positioned within protective tube 18. Swage-type fitting 20 is coupled to first end portion 22 of probe case 14 to sealingly couple protective tube 18 to probe case 14. Probe cable 24 extends through protective tube 18 and fitting 20 into cavity 16 defined by probe case 14.

In the exemplary embodiment, inspection device 10 includes a plurality of sealing components, such as O-rings 40 and 42, to sealing couple first tip assembly 30 and second tip assembly 36 within probe case 14 to facilitate preventing or limiting undesirable leakage of pressurized water into cavity 16, while allowing inspection and/or measurement of machinery components in pressurized environments, such as underwater environments at or near a hydroelectric power dam. More specifically, the sealing components, i.e. at least one O-ring 40, facilitate preventing or limiting undesirable leakage of pressurized water into cavity 16 at an interface between first tip assembly 30 and second tip assembly 36, and the other sealing components, i.e., at least one O-ring 42, facilitates preventing or limiting undesirable leakage of pressurized water into cavity 16 at an interface between first tip assembly 30 and probe case 14.

In the exemplary embodiment, inspection device 10 also includes swage-type fitting 20 to further facilitate preventing or limiting undesirable leakage of pressurized water into cavity 16 at an interface between protective tube 18 and fitting 20 and/or at an interface between fitting 20 and first end 22 of probe case 14.

The above-described eddy current inspection device is suitable for use in pressurized environments, such as pressurized liquid or underwater environments, to inspect and/or monitor rotating machinery components in a cost-effective and reliable manner. More specifically, the eddy current inspection device includes sealing components, such as O-ring seals, positioned about one or more of the tip assemblies to sealingly couple the tip assemblies within the probe case and prevent or limit undesirable pressurized liquid leakage into the probe case at an interface between tip assemblies and/or at-an interface between the tip assemblies and the probe case.

Exemplary embodiments of an eddy current inspection device are described above in detail. The inspection device components illustrated herein are not limited to the specific embodiments described herein, but rather, components of the eddy current inspection device may be utilized independently and separately from other components described herein. For example, the components described above may also be used in combination with other proximity probe inspection devices and/or systems.

While the invention has been described in terms of various specific embodiments, those skilled in the art will recognize that the invention can be practiced with modification within the spirit and scope of the claims.

What is claimed is:

1. A method for assembling an eddy current inspection device, said method comprising:
   positioning a first tip assembly at least partially within a cavity defined by a proximity probe case, wherein the first tip assembly includes a bore defined therethrough;
   sealingly coupling the first tip assembly to the proximity probe case;
   positioning a second tip assembly at least partially within the cavity; and
   sealingly coupling the second tip assembly to the first tip assembly.

2. A method in accordance with claim 1 wherein sealing coupling the first tip assembly to the proximity probe case further comprises positioning at least one sealing component about the first tip assembly to facilitate sealing between an outer surface of the first tip assembly and an inner wall surface of the proximity probe case.

3. A method in accordance with claim 1 wherein positioning a second tip assembly within the cavity further comprises seating the second tip assembly within the bore.

4. A method in accordance with claim 1 wherein sealing coupling the second tip assembly to the first tip assembly further comprises positioning at least one sealing component about the first tip assembly to facilitate sealing between an outer surface of the first tip assembly and an inner wall surface of the second tip assembly.

5. A method in accordance with claim 1 wherein sealing coupling the second tip assembly to the first tip assembly further comprises coupling a flange of the second tip assembly against an outer surface of the first tip assembly.

6. A method in accordance with claim 1 further comprising electrically coupling a cable to the second tip assembly such that the cable extends through the bore.

7. A method in accordance with claim 6 further comprising sealingly coupling a tube to the proximity probe case such that the cable extends through the tube.

8. A method in accordance with claim 7 wherein coupling a tube to the proximity probe case further comprises coupling a swage-type fitting to a first end of the proximity probe case to sealingly couple the tube to the proximity probe case, wherein the cable extends through the tube and the fitting into the cavity defined by the proximity probe case.

9. A proximity probe coupled in communication with an electronic circuit and positionable adjacent to a rotating machinery component, said proximity probe configured to generate a signal indicative of a gap between rotating machinery components, said proximity probe comprising:
a case defining a cavity;
a first tip assembly at least partially positioned within said cavity and sealingly coupled to said case; and
a second tip assembly coupled to a probe cable and at least partially positioned within said cavity, said second tip assembly sealingly coupled to said first tip assembly.

10. A proximity probe in accordance with claim 9 wherein said first tip assembly defines a bore through which the probe cable extends, said second tip assembly seated within said bore.

11. A proximity probe in accordance with claim 9 wherein said second tip assembly further comprises a circumferential flange coupling against an outer surface of said first tip assembly.

12. A proximity probe in accordance with claim 9 further comprising at least one first sealing component positioned about said first tip assembly to facilitate sealing a space defined between an outer surface of said first tip assembly and an inner wall surface of said second tip assembly.

13. A proximity probe in accordance with claim 12 wherein said at least one sealing component comprises at least one O-ring.

14. A proximity probe in accordance with claim 12 further comprising at least one second sealing component positioned about said first tip assembly to facilitate sealing a space defined between said outer surface of said first tip assembly and an inner wall surface of said probe case.

15. A proximity probe in accordance with claim 14 wherein said at least one second sealing component comprises at least one O-ring.

16. A proximity probe in accordance with claim 9 further comprising a swage-type fitting coupled to said probe case and configured to facilitate preventing undesirable leakage of pressurized water into said cavity through an interface defined between a protective tube positioned about the probe cable and said fitting.

17. An eddy current (EC) inspection device for use with rotating machinery components, said EC inspection device comprising:
a proximity probe coupled in communication with an electronic circuit and positionable adjacent to the rotating machinery component, said probe configured to produce eddy currents to generate a signal indicative of a gap between rotating machinery components, said proximity probe comprising:
a proximity probe case defining a cavity;
a first tip assembly at least partially positioned within said cavity and sealingly coupled to said proximity probe case; and
a second tip assembly coupled to a probe cable and at least partially positioned within said cavity, said second tip assembly sealingly coupled to said first tip assembly.

18. An EC inspection device in accordance with claim 17 wherein said first tip assembly defines a bore through which the probe cable extends, said second tip assembly seated within said bore.

19. An EC inspection device in accordance with claim 17 wherein said second tip assembly further comprises a circumferential flange coupled against an outer surface of said first tip assembly.

20. An EC inspection device in accordance with claim 17 further comprising:
at least one first sealing component positioned about said first tip assembly to facilitate sealing a space defined between an outer surface of said first tip assembly and an inner wall surface of said second tip assembly; and
at least one second sealing component positioned about said first tip assembly to facilitate sealing between said outer surface of said first tip assembly and an inner wall surface of said probe case defining said cavity.

\* \* \* \* \*